United States Patent
He et al.

(10) Patent No.: US 6,393,190 B1
(45) Date of Patent: May 21, 2002

(54) CHROMOPHORES FOR POLYMERIC THIN FILMS AND OPTICAL WAVEGUIDES AND DEVICES COMPRISING THE SAME

(75) Inventors: Mingqian He, Painted Post; Thomas M. Leslie, Horseheads, both of NY (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 09/675,966

(22) Filed: Sep. 29, 2000

Related U.S. Application Data

(63) Continuation-in-part of application No. 09/595,221, filed on Jun. 16, 2000.

(51) Int. Cl.[7] .................. G02B 6/10; B32B 27/28; G03C 1/73
(52) U.S. Cl. ............... 385/130; 385/143; 252/582; 428/412; 428/423.1; 428/473.5
(58) Field of Search .................. 385/129, 130, 385/141–143; 428/412, 423.1, 473.5; 252/582, 583, 586

(56) References Cited

U.S. PATENT DOCUMENTS

| | | | |
|---|---|---|---|
| 4,014,951 A | 3/1977 | Naf et al. ............... 585/600 |
| 4,767,169 A | 8/1988 | Teng et al. ............ 350/96.14 |
| 4,795,664 A | 1/1989 | DeMartino ............... 428/1 |
| 4,810,338 A | 3/1989 | DeMartino et al. .... 204/157.88 |
| 4,936,645 A | 6/1990 | Yoon et al. ........... 350/96.14 |
| 5,006,285 A | 4/1991 | Thackara et al. .......... 264/1.3 |
| 5,044,725 A | 9/1991 | DeMartino et al. ........ 385/130 |
| 5,106,211 A | 4/1992 | Chiang et al. ............ 385/132 |
| 5,133,037 A | 7/1992 | Yoon et al. ............. 385/132 |
| 5,170,461 A | 12/1992 | Yoon et al. ............. 385/130 |
| 5,187,234 A | 2/1993 | Leslie et al. ............ 525/276 |
| 5,196,509 A | 3/1993 | Allen ................... 528/331 |
| 5,247,042 A | 9/1993 | Allen et al. ............. 526/310 |
| 5,290,630 A * | 3/1994 | Devonald et al. .......... 428/333 |
| 5,326,661 A | 7/1994 | Sansone et al. ............ 430/20 |
| 6,057,316 A | 5/2000 | Wrobel et al. ........... 514/224.5 |
| 6,067,186 A | 5/2000 | Dalton et al. ............ 359/321 |
| 6,114,031 A * | 9/2000 | Roberts et al. ........... 428/333 |

FOREIGN PATENT DOCUMENTS

| JP | 3-101671 A | 4/1991 |
|---|---|---|
| WO | WO 98/56749 | 12/1998 |

OTHER PUBLICATIONS

Advanced Organic Chemistry, 3rd Ed., Jerry March, 1985, Table 1, pp. 220–222.

Melikian, G. et al.; Synthesis of Substituted Dicyanomethylendihydrofurans, Synthetic Communications, 25(19), pp. 3045–3051 (1995).

Wang et al., "Design, Synthesis and Characterization of a Novel Substituted Dicyanomethylendihydrofuran Based High–β NLO Chromophore and Its Polymers with Exceptionally High Electro–Optic Coefficients," *Polymer Preprints*, 39(2):1065–1066 Aug. (1998).

Zhang et al., "A Novel Trilinkable High $\mu\beta$ NLO Chromophore for Polymeric Electro–optic Material With Enhanced Thermal Stability," *Polymer Preprints*, 40:156–157 (1999).

Ren et al., "A Trifunctionalized High $\mu\beta$ Chromophore and Its Polyurethane Network With Enhanced NLO Alignment Stability for Electro–optic Device Applications," *Polymer Preprints*, 40:160–161 (1999).

Ren, "Electro Active Polymer Thin Films for Fabrication of Ultra–high Bandwidth Integrated Electro–optic Modulators," Ph.D. Thesis, University of Southern California Aug. (1999).

Todorova et al., "New NLO Chromophores Based on 2–amino–1,1,3–tricyano–1–propene Acceptor," *Polymer Materials: Science and Engineering*, 83:256–257 Aug. (2000).

Reddy et al., "Vilsmeier Reaction on Some 6 & 7–Methoxy–1–tetralols," *Indian Journal of Chemistry*, 20B:100–103 (1981).

* cited by examiner

Primary Examiner—John D. Lee
(74) Attorney, Agent, or Firm—Angela N. Nwaneri; Peter R. Rogalskyj

(57) ABSTRACT

The present invention is directed to chromophores having novel electron withdrawing groups and novel bivalent cyclic bridges and to optical waveguides and optical devices having polymeric thin films which contain the novel chromophores.

78 Claims, No Drawings

CHROMOPHORES FOR POLYMERIC THIN FILMS AND OPTICAL WAVEGUIDES AND DEVICES COMPRISING THE SAME

This application is a continuation-in-part of co-pending U.S. patent application Ser. No. 09/595,221, filed Jun. 16, 2000.

FIELD OF THE INVENTION

The present invention relates to chromophores which can be used in the preparation of polymeric thin films for waveguide media, and to optical waveguides and devices comprising the chromophores.

BACKGROUND OF THE INVENTION

Thin films of organic or polymeric materials with large second order nonlinearities in combination with silicon-based electronic circuitry can be used in systems for laser modulation and deflection, information control in optical circuitry, as well as in numerous other waveguide applications. In addition, novel processes through third order nonlinearity such as degenerate four-wave mixing, whereby real-time processing of optical fields occurs, have utility in such diverse fields as optical communications and integrated circuit fabrication. The utility of organic materials with large second order and third order nonlinearities for very high frequency application contrasts with the bandwidth limitations of conventional inorganic electrooptic materials currently in use.

Numerous optically responsive monomers and polymers have been developed for use in organic materials which, in turn, can be used in the waveguide applications described above. For example, U.S. Pat. No. 5,044,725, which is incorporated herein by reference in its entirety, describes numerous polymer compositions which provide suitable nonlinear optical response. U.S. Pat. No. 5,044,725 describes, for example, a preferred polymer composition comprising an organic chromophore containing an electron donating group and an electron withdrawing group at opposing termini of a bridge.

Synthesis of high performance organic, high $\mu\beta$ electro-optic chromophores must be accomplished in order to make polymer-based electro-optic waveguides and devices. The synthesis of electro-optic chromophore bridge compounds and donor-bridge compounds for organic nonlinear optical applications are generally known in the art. Although some chromophores have been reported in the literature, many of them have shown several and sometimes severe problems ranging from thermal instability, insolubility in the polymer, photodegradability, exhibition of a broad absorption band into the wavelength region of interest, and large birefringence upon poling.

Most recently, U.S. Pat. No. 6,067,186 (the '186 patent), disclosed a class of organic chromophors which can result in hardened electro-optic polymers suitable for electro-optic modulators and other devices such as optical switch.

There continues to be a need for suitable electro-optic chromophores with improved properties.

SUMMARY OF THE INVENTION

The present invention is directed, in part, to compounds which can serve as chromophores in, for example, thin films for optical waveguides and optical devices. These are compounds represented by Formula I:

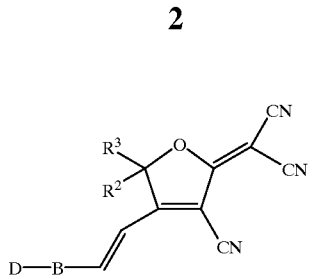

(I)

wherein:
D is an electron donating group;
B comprises at least one bivalent ring; and
$R^2$ and $R^3$ each, independently, are selected from the group consisting of substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is 1–10. Alternatively, $R^2$ and $R^3$ can be selected from substituted or unsubstituted $C_2$–$C_{10}$ alkyl, provided that when $R^2$ and $R^3$ are both selected from substituted or unsubstituted $C_1$–$C_1$ alkyl the following condition is also met: $R^2 \neq R^3$. More preferably, chromophores of the invention have Formula I':

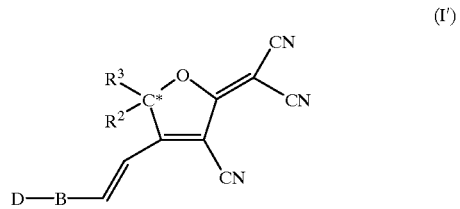

(I')

where:
$R^2$ and $R^3$ are further characterized in that they define a ring in which * denotes a spiro junction, or where * denotes a chiral center; D and B have the definitions given above; and $R^2$ and $R^3$ each, independently, are either, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocyclic, substituted or unsubstituted heterocyclic, substituted or unsubstituted cyclohexyl, or $(CH_2)_n$—O—$(CH_2)_n$, where n is 1–10.

In still another aspect of the invention, the chromophores comprise novel cyclic bridges comprising at least one bivalent aromatic ring. Preferred compounds of the invention have Formula II:

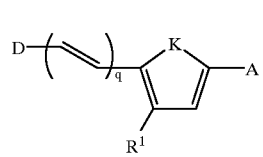

II wherein D is an electron donating group; A is an electron withdrawing group; K is O or S;

$R^1$ is $-Q-C_nH_{2n+1}$, $-Q-(CH_2)_aCC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S; and q is 1, 2, or 3.

Other preferred compounds of the invention have Formula III:

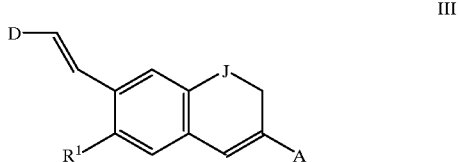

(III)

wherein D is an electron donating group; A is an electron withdrawing group; J is $CH_2$, O or S; $R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S.

In other embodiments of the invention, the chromophores comprise novel cyclic bridges comprising at least one bivalent or conjugated ring structure, such as an aromatic ring, and novel electron withdrawing groups. Such compounds are generally represented by the structure of Formula IV:

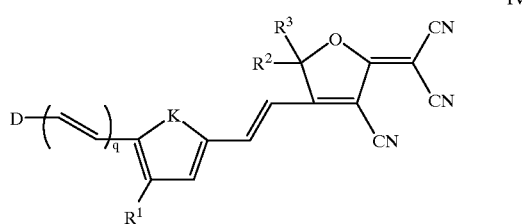

IV wherein D is an electron donating group; K is O or S; $R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S; q is 1, 2, or 3; and $R^2$ and $R^3$ each, independently, are either substituted or unsubstituted $C_1-C_{10}$ alkyl, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, or $(CH_2)_n-O-(CH_2)_n$ where n is 1–10. Alternatively, $R^2$ and $R^3$ together form a ring structure or a substituted ring structure. Preferred compounds of this embodiment are represented by the structure of Formula IV':

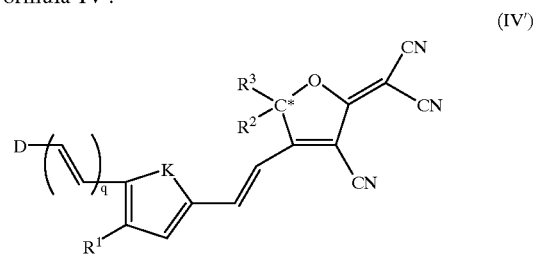

(IV')

where:
$R^2$ and $R^3$ are further characterized in that they define a ring in which * denotes a spiro junction, or where * denotes a chiral center.

Other useful compounds of the invention have Formula V:

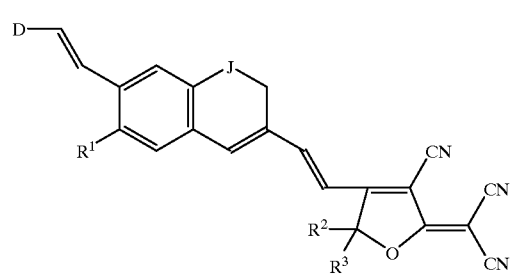

V wherein D is an electron donating group; J is $CH_2$, O or S; $R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S; and $R^2$ and $R^3$ each, independently, are either H, substituted or unsubstituted $C_1-C_{10}$ alkyl, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, or $(CH_2)_n-O-(CH_2)_n$ where n is 1–10. Alternatively, $R^2$ and $R^3$ together form a ring structure or a substituted ring structure. Preferred chromophores of this embodiment include compounds of Formula (V'):

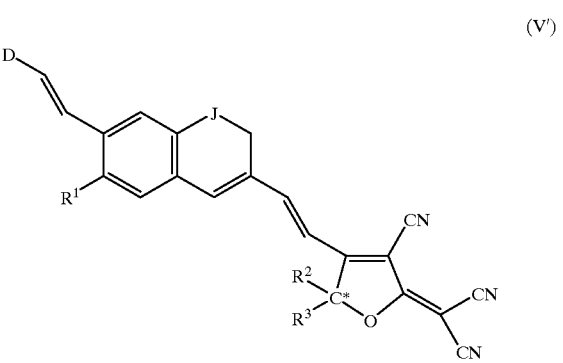

(V')

where:
$R^2$ and $R^3$ are further characterized in that they define a ring in which * denotes a spiro junction, or where * denotes a chiral center.

The present invention is also directed to optical waveguides comprising a thin film medium having Formula VI:

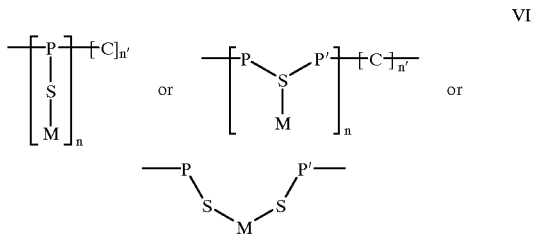

VI wherein P and P' are polymer main chain units, which can be the same mer unit or different mer unit, and C is a comonomer unit where n is an integer greater than zero and n' is 0 or an integer greater than zero; S is a pendant spacer group having a linear chain length of between about 2–12 atoms. M is a compound having either Formula I, Formula II, Formula III, Formula IV, or Formula V, as described above.

The phrase "electron donating group" is used synonymously with "electron donator" and refers to substituents which contribute electron density to the π-electron system when the conjugated electron structure is polarized by the input of electromagnetic energy.

The phrase "electron withdrawing group" is used synonymously with "electron accepting group" and "electron acceptor" and refers to electronegative organic compounds or substituents which attract electron density from the π-electron system when the conjugated electron structure is polarized by the input of electromagnetic energy.

The term "chromophore" as used herein refers to an optical compound comprising an electron donating group and an electron withdrawing group at opposing termini of a conjugated π-electron system.

The phrase "cyclic bridge" is used to refer to bivalent cyclic structures which serve to couple the electron donating and withdrawing groups.

The present invention is also directed to optical devices comprising the optical waveguides described above.

DESCRIPTION OF PREFERRED EMBODIMENTS OF THE INVENTION

The present invention is directed, in part, to novel electro-optic chromophores which have utility in organic nonlinear optical applications such as polymeric thin films for optical waveguides and optical devices. Such polymeric thin films are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety.

The inventive chromophores have several advantageous features which are not found in other known or commercially available chromophores. For example, we have found that the introduction of a chiral center, preferably in the acceptor portion of the molecule, and more preferably as a racemic mixture, greatly increases the chromophore's solubility. We have found that solubility is enhanced the greater the structural or functional differences between $R^2$ and $R^3$. For example, we have observed significantly enhanced solubility when one of $R^2$ or $R^3$ is a chain and the other is a ring structure; or when one is a short chain (up to three carbons), and the other is a long chain (say, $C_4$–$C_{18}$). This increased solubility in turn can lead to an enhanced nonlinearity of the final material in many cases. It is known that the introduction of long chain alkane groups increase the solubility of chromophores, and that as the number and size of the alkane moieties increase, both the solubility and bulk material nonlinearity are greatly improved. The chromophores of the present invention have an enhanced solubility over the dimethyl types of the prior art.

While there may be other factors contributing to this improved property, we have found that one major difference between the inventive acceptors and those of the prior art is the presence of chiral centers in the inventive acceptors. It is known that the physical characteristics like melting point and solubility are different for the pure enantiomer than for the racemic mixture. Several examples of this difference exist. For example, pure chiral (D) lycine has a melting point of 218 C and is very soluble at room temperature. The racimate has a melting point of 170 C and is considered infinitely soluble in room temperature water. Also, pure enantiomers of Mandelic acid have a melting point of 133 C while the racimate has a melting pint of 120 C. (R)-(+)-Mandelonirile has a melting point of 29 C while the racimate is an oil at room temperature.

In the specific chemistry of the present invention, the chiral centers do not form a single chiral compound but rather a mixture of racemic enantiomers, which when introduced into chromophores increase the solubility of the chromophores due to a depression of the melting point. In fact, we have found that the inventive compounds tend to form glassy solids rather than crystalline materials. Without intending to be bound by theory, we believe that the present chemistry results in improvements in the nonlinearity of the bulk polymer because of the incorporation of a racemic chiral center in the chromophores.

The electro-optic chromophores of the invention exhibit thermal stability to temperatures from 260° C. to 310° C. These chromophores also show great solubility in most common organic solvents and, thus, are useful when used as a guest additive in most polymer films for waveguides. In addition, under intense UV-irradiation (365 nm, dosage 3 $J/cm^2$ up to 13 minutes), the chromophores of the invention show no changes of the UV-VIS-NIR spectrum, which indicates that the chromophores are photostable. The chromophores also demonstrate an adjustable absorption band away from normal communications wavelenghts, which can be very important for reducing optical loss at communication wavelengths. The chromophores of the invention have significant three-dimensional design which can prevent chromophore-chromophore anti-parallel stacking. Because of the flexible side chain substitutions, the chromophores of the invention show significantly reduced birefringence losses. In some of the chromophores of the invention, there is unique regiospecific substitution on the bridging thiophene ring, which allows the electron acceptor to more easily access the conjugated π-system of the bridge and allows the molecule backbone to be flatter. In addition, some of the preferred chromophores of the invention have hydroxyl groups on the electron donor termini in order to easily process the chromophore into hydroxyl compatible organic and inorganic polymer reactions to make soluble chromophores, polymers and copolymers, as well as can be used to make highly soluble "guest" chromophores for guest-host applications.

The present invention is directed, in part, to compounds which can be employed as chromophores in polymeric thin films for optical waveguides. In preferred embodiments of the invention, such compounds comprise novel electron withdrawing groups having Formula I:

I

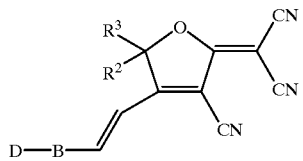

where: D is an electron donating group. Preferred electron donating groups are described in, for example, U.S. Pat. Nos. 5,044,725, 4,795,664, 5,247,042, 5,196,509, 4,810, 338, 4,936,645, 4,767,169, 5,326,661, 5,187,234, 5,170,461, 5,133,037, 5,106,211, and 5,006,285, each of which is incorporated herein by reference in its entirety. Preferably, D is selected from the group consisting of, but not limited to, phenyl ring(s) substituted in the para position by, for example, amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, 1,2,3,4-tetrahydroquinolinyl, and the like. The most preferred electron donating groups are substituted and unsubstituted-phenyl-$N(CH_2CH_2OH)_2$.

B is a cyclic bridge which couples the electron withdrawing group and the electron donating group. Preferably, B is at least one bivalent ring. Preferred cyclic bridges comprise one or a plurality of bivalent rings. Preferred bivalent rings which can be employed as cyclic bridges in the present application are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety. Ring B can be aromatic or non-aromatic. Preferably, B is selected from the group consisting of, but not limited to,

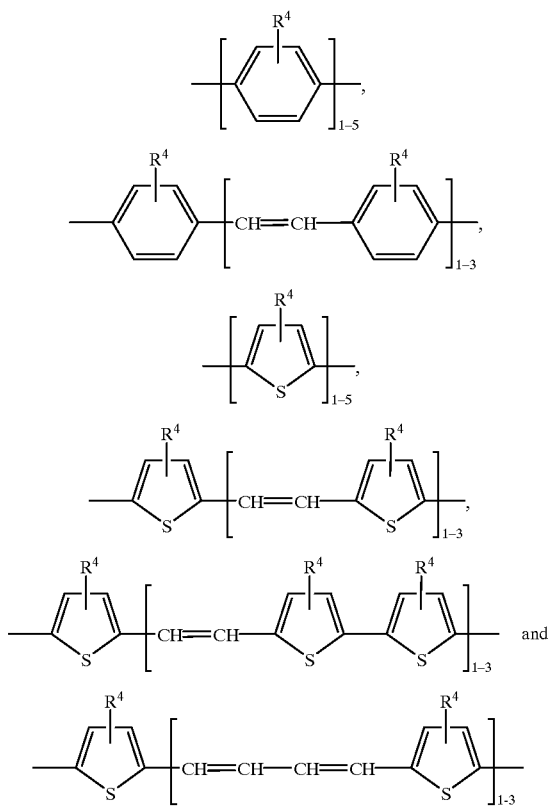

where $R^4$ is H, OH, $C_1$–$C_{10}$ alkyl, alkenyl, or alkynyl, halogen, and the like. $R^4$ can also be —Q—$C_nH_{2n+1}$, —Q—$(CH_2)_aC_nF_{2n+1}$, —Q—$CH_2OCH_2C_nF_{2n+1}$, —Q—$CH_2SCH_2CC_nF_{2n+1}$, —Q—$CH_2OCH_2CF_3$, or —Q—$CH_2SCH_2CF_3$, where n is 1–10, a is 0–10, and Q is absent, O or S; and q is 1, 2, or 3.

$R^2$ and $R^3$ each, independently, are selected from the group consisting of, but not limited to, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, $(CH_2)_n$—O—$(CH_2)_n$ where n is 1–10, and the like. "$C_1$–$C_{10}$" refers to $C_1$, $C_2$, $C_3$, $C_4$, $C_5$, $C_6$, $C_7$, $C_8$, $C_9$, $C_{10}$, and all combinations of ranges thereof. Preferably, when $R^2$ and $R^3$ are both selected from substituted or unsubstituted $C_1$–$C_{10}$ alkyl the following condition is also met: $R^2 \neq R^3$. More preferably, $R^2$ and $R^3$ define a ring in which * denotes a spiro junction, or where * denotes a chiral center.

The substituted alkyl, alkenyl, alkynyl, carbocyclic, and heterocyclic groups can comprise one or a plurality of substituents including, for example, fluorine, chlorine, D, and the like. In addition, the heterocyclic groups can comprise O, N, S, and the like.

The aryl groups preferably include, but are not limited to, benzyl, phenyl, fluorenyl, and naphthyl. The aryl groups, carbocycles, heterocycles, and cyclohexyl can also be substituted by one or a plurality of substituents including, for example, D, halides, including fluorine, chlorine and bromine. The alkylaryl groups preferably comprise $C_1$–$C_{10}$ alkyl and the substituted alkylaryl groups comprise the substitutions for the alkyl and aryl groups described above.

In more preferred embodiments of the invention, $R^2$ and $R^3$ each, independently, are selected from the group consisting of benzyl, carbocycle, heterocycle, cyclohexyl, phenyl, cycloalkyl, cycloalkenyl, and substituted phenyl. Additional moieties for $R^2$ and/or $R^3$, independently, include, but are not limited to the following:

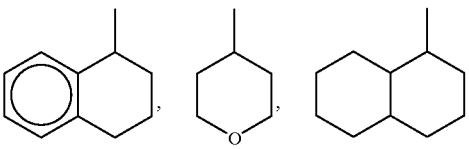

and the like.

In even more preferred embodiments of the invention, one of $R^2$ and $R^3$ is $CH_3$ and the other of $R^2$ and $R^3$ is a substituted phenyl. Preferably, the substituted phenyl is selected from the group consisting of, but not limited to:

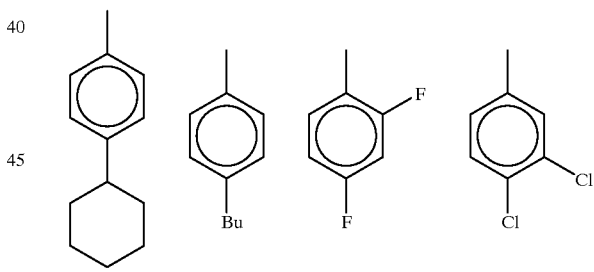

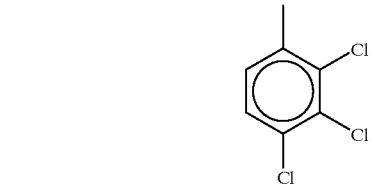

and the like.

Alternatively, $R^2$ and $R^3$ together form a ring structure or a substituted ring structure from 3 to 7 atoms total with 5 or 6 atoms being preferred. Preferably, the ring structure is substituted or unsubstituted carbocycle, substituted or unsubstituted heterocycle, or substituted or unsubstituted cyclohexyl or cyclopentyl. The substituted ring structure can comprise substituents including, but not limited to, halides, including fluorine, chlorine and bromine. A preferred compound having a ring structure formed by $R^2$ and $R^3$ comprises

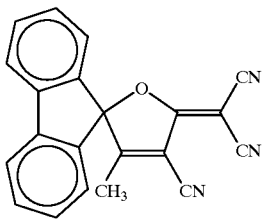

The electron withdrawing groups of the present invention are preferably prepared according to Scheme I:

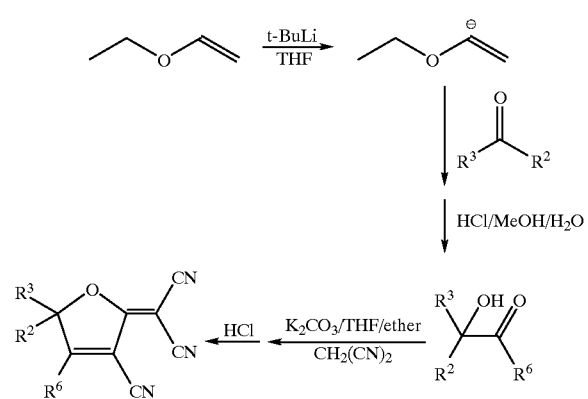

Scheme I

Compounds having Formula I are preferably prepared by the following steps depicted in Scheme I: a) providing an alkylvinylether, b) contacting the alkylvinylether with a strong base to form a first intermediate compound, c) contacting the first intermediate compound with a ketone to form a second intermediate compound, and d) reacting the second intermediate compound with dicyanomethane in the presence of a second base to form an electron withdrawing group portion of a compound having Formula I. Each of the above mentioned steps is described in greater detail below.

In preferred embodiments of the invention, an alkylvinylether in a solvent is the starting material. The solvent is, preferably, tetrahydrofuran (THF), 1,4-dioxane, or the like. Although the alkylvinylether depicted in Scheme I is ethylvinylether, other alkylvinylethers can be used. The alkylvinylether preferably comprises the formula $CH_3$—$(CH_2)_x$—O—CH=$CHR^6$, where x is 1–3 and $R^6$ is $C_1$–$C_4$ alkyl. Most preferably, the alkylvinylether is methylvinylether or ethylvinylether.

The alkylvinylether is contacted with a strong base to form a first intermediate compound. Preferably, the strong base has a $pK_a$ greater than the ethylinic C—H bond α to the oxygen function of the alkylvinylether. For example, see Advanced Organic Chemistry, Third Ed., Jerry March, 1985, Table 1, pp. 220–222. In preferred embodiments of the invention, the strong base is an alkyl lithium, or an alkali metal salt of an alkyl anion, including, but not limited to, t-BuLi or sec-BuLi. The alkylvinylether is preferably contacted with the strong base between about –70° C. and –85° C., most preferably at about –78° C.

The first intermediate compound is contacted with a ketone and an acid/alcohol/water solution to form a second intermediate compound. Numerous acid/alcohol/water solutions known to those skilled in the art can be used in the present invention. The acid/alcohol/water solution is preferably HCl/MeOH/$H_2O$, HBr/EtOH/$H_2O$, or $H_2SO4$/EtOH/$H_2O$. Preferably, the contacting is at room temperature. Preferably, the pH is adjusted between 1 and 4.

Preferably, the ketone comprises $R^3$—C(=O)$R^2$, wherein $R^2$ and $R^3$ each, independently, are selected from the group consisting of, substituted and unsubstituted $C_{10}$ alkyl, substituted and unsubstituted $C_1$-$C_{10}$ alkenyl, substituted and unsubstituted $C_{10}$ alkynyl, substituted and unsubstituted aryl, substituted and unsubstituted alkylaryl, substituted and unsubstituted carbocycle, substituted and unsubstituted heterocycle, substituted and unsubstituted cyclohexyl, and $(CH_2)_n$—O—$(CH_2)_n$ where n is 1–10.

"$C_1$-$C_{10}$" refers to $C_1$, $C_2$, $C_3$, $C_4$, $C_5$, $C_6$, $C_7$, $C_8$, $C_9$, $C_{10}$, and all combinations of ranges thereof.

Preferably, the C=C and C≡C bonds of the alkenyl and alkynyl groups are not immediately adjacent or conjugated to the carbonyl group of the ketone compound.

The substituted alkyl, alkenyl, alkynyl, carbocyclic, and heterocyclic groups can comprise one or a plurality of substituents including, for example, fluorine, chlorine, D, and the like. In addition, the heterocyclic groups can comprise O, N, S, and the like.

The aryl groups preferably include, but are not limited to, benzyl, phenyl, fluorenyl, and naphthyl. The aryl groups, carbocycles, heterocycles, and cyclohexyl can also be substituted by one or a plurality of substituents including, for example, D, halides, including fluorine, chlorine and bromine. The alkylaryl groups preferably comprise $C_1$–$C_{10}$ alkyl and the substituted alkylaryl groups comprise the substitutions for the alkyl and aryl groups described above.

In more preferred embodiments of the invention, $R^2$ and $R^3$ each, independently, are selected from the group consisting of benzyl, carbocycle, heterocycle, cyclohexyl, phenyl, cycloalkyl, cycloalkenyl, and substituted phenyl. Additional moieties for $R^2$ and/or $R^3$, independently, include, but are not limited to the following:

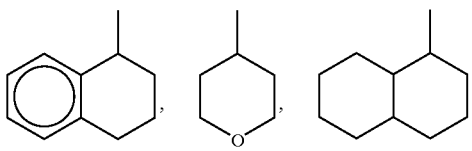

and the like.

In even more preferred embodiments of the invention, one of $R^2$ and $R^3$ is $CH_3$ and the other of $R^2$ and $R^3$ is a substituted phenyl. Preferably, the substituted phenyl is selected from the group consisting of, but not limited to:

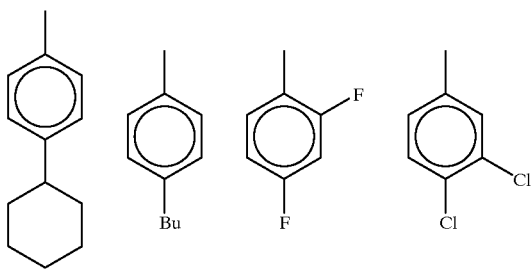

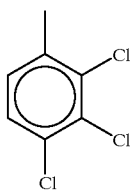

and the like.

Alternatively, $R^2$ and $R^3$ together form a ring structure or a substituted ring structure from 3 to 7 atoms total with 5 or 6 atoms being preferred. Preferably, the ring structure is substituted or unsubstituted carbocycle, substituted or unsubstituted heterocycle, or substituted or unsubstituted cyclohexyl or cyclopentyl. The substituted ring structure can comprise substituents including, but not limited to, halides, including fluorine, chlorine and bromine. A preferred compound having a ring structure formed by $R^2$ and $R^3$ comprises

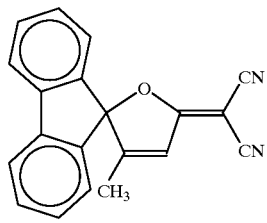

The second intermediate compound is reacted with dicyanomethane in the presence of a second base to form the electron withdrawing group portion of a compound having Formula I. The second base is preferably a metal alkoxide including, but not limited to, $NaOC_2H_5$. After contacting the second intermediate compound with dicyanomethane in the presence of a second base, dilute acid such as, for example, HCl, is added for neutralization of the resultant electron withdrawing group.

The electron withdrawing group comprises $R^6$ which is preferably selected from the group consisting of unbranched substituted or unsubstituted $C_1$–$C_4$ alkyl, unbranched substituted or unsubstituted $C_2$–$C_4$ alkenyl, unbranched substituted or unsubstituted $C_2$–$C_4$ alkynyl. The substituted alkyl, alkenyl, and alkynyl groups can comprise one or a plurality of substituents including, for example, fluorine. In preferred embodiments of the invention, $R^6$ is selected from the group consisting of unbranched $C_1$–$C_4$ alkyl, $C_1$–$C_4$ alkenyl, and $C_1$–$C_4$ alkynyl. In more preferred embodiments of the invention, $R^6$ is $CH_3$.

The present invention is also directed, in part, to compounds which can be employed as chromophores in polymeric thin films for optical waveguides wherein the compounds comprise novel bridge groups which couple the electron withdrawing and donating groups of the chromophore. Preferred compounds of the invention have Formula II:

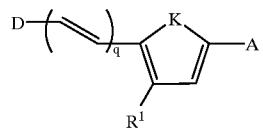

D is an electron donating group. Preferred electron donating groups are described above.

A is an electron withdrawing group. Preferred electron withdrawing groups are described in, for example, U.S. Pat. Nos. 5,044,725, 4,795,664, 5,247,042, 5,196,509, 4,810, 338, 4,936,645, 4,767,169, 5,326,661, 5,187,234, 5,170,461, 5,133,037, 5,106,211, and 5,006,285, each of which is incorporated herein by reference in its entirety. Preferably, A is selected from the group of molecular units containing, but not limited to, nitro, cyano, haloalkyl, acyl, carboxy, aryloxy, carboxamido, alkoxysulfonyl, aryloxysulfonyl, $-CH=C(CN)_2$, $-C(CN)=C(CN)_2$, $SO_2CF_3$, alkanoyloxy,

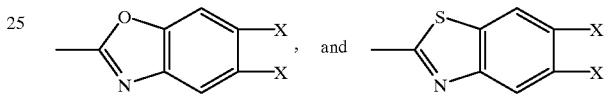

where X is H, D, F, CN, $NO_2$, or $CF_3$.

$R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q preferably is either absent or, when present, O or S; q is 1, 2, or 3. More preferably, $R^1$ is $C_4$–$C_{10}$ or fluorine substituted $C_4$–$C_{10}$.

A compound having Formula II can be prepared using a thiophene cyclic bridge which preferably comprises Formula VII:

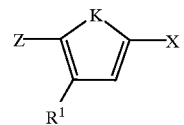

Preferably, K is O or S.

Preferably, $R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q preferably is either absent or, when present, O or S. Other halogens or deuterium can be used in place of F. In more preferred embodiments of the invention, $R^1$ is $C_4$–$C_{10}$ or fluorine substituted $C_4$–$C_{10}$.

X preferably has the formula $-(CH=CH)_b-C(=O)H$, where b is 0–3. The terminal aldehyde group serves as the preferred site of reaction with electron withdrawing groups. In more preferred embodiments of the invention, b is 0 so that X is $-C(=O)H$.

Z is a chemical group that is capable of being linked to a donor and includes, but is not limited to, Br, I, $-CH_2-Br$, $-CH_2-OH$, $-CH_3$, $-C(=O)H$, and the like. Those skilled in the art can use additional groups known to those skilled in the art to couple a bridge compound to a donor.

Another Z group that can be used to link a bridge compound to a donor is

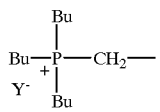

where Y⁻ is a counter ion including, but not limited to, Br⁻ or Cl⁻.

In other embodiments of the invention, preferred compounds of the invention have Formula III:

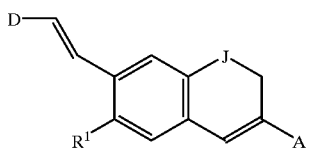

D is an electron donating group and A is an electron withdrawing group as described above. J is $CH_2$, O or S.

$R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S.

More preferably, $R^1$ is $C_4-C_{10}$ or fluorine substituted $C_4-C_{10}$.

A compound having Formula IV can be prepared using a dihydronaphthyl cyclic bridge which preferably comprises Formula VIII:

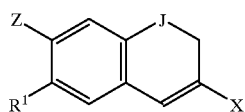

Preferably, J is $CH_2$, O or S.

Preferably, $R^1$ is H, $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2+1}$, $-Q-CH_2OCH_2CF_3$, or $-Q-CH_2SCH_2CF_3$, where n is 1–10, a is 0–10, and Q is absent, O or S. Other halogens can be used in place of F. In more preferred embodiments of the invention, $R^1$ is $C_4-C_{10}$ or fluorine substituted $C_4-C_{10}$.

X preferably has the formula (C=O)H or C=CH(—CH=CH)$_d$—C(=O)H, where d is 0–3. The terminal aldehyde or ketone group serves as the preferred site of reaction with electron withdrawing groups. In more preferred embodiments of the invention, X is (C=O)H.

Z is a chemical group that is capable of being linked to a donor, as described above.

The present invention is also directed to compounds which can be employed as chromophores in polymeric thin films for optical waveguides wherein the compounds comprise novel bridge groups and novel electron withdrawing groups, and are represented by Formula IV:

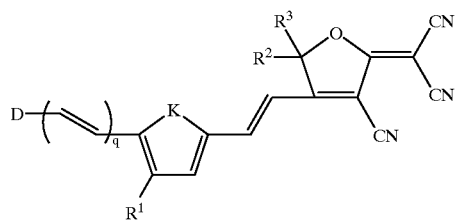

where, K is O or S; and
$R^1$ is $-Q-C_nH_{2n+1}$, $-Q-(CH_2)_aC_nF_{2n+1}$, $-Q-CH_2OCH_2C_nF_{2+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S, and q is 1, 2, or 3. In more preferred embodiments of the invention, $R^1$ is $C_4-C_{10}$ or fluorine substituted $C_4-C_{10}$. More preferred compounds of this embodiment of the invention are represented by Formula IV':

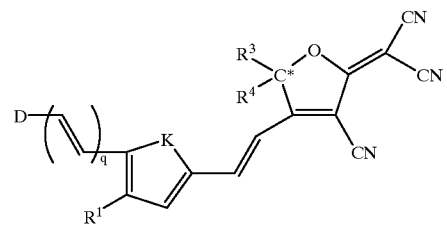

where:
$R^2$ and $R^3$ are further characterized in that they define a ring in which * denotes a spiro junction, or where * denotes a chiral center.

Preferably, $R^2$ and $R^3$ each, independently, are selected from the group consisting of, but not limited to, substituted or unsubstituted $C_1-C_{10}$ alkyl, substituted or unsubstituted $C_2-C_{10}$ alkenyl, substituted or unsubstituted $C_2-C_{10}$ alkenyl, substituted or unsubstituted aryl, substituted or unsubstituted alkylaryl, substituted or unsubstituted carbocycle, substituted or unsubstituted heterocycle, substituted or unsubstituted cyclohexyl, $(CH_2)_n-O-(CH_2)_n$ where n is 1–10, and the like. More preferably, $R^2$ and $R^3$ each, independently, are selected from the group consisting of substituted or unsubstituted aryl, substituted or unsubstituted alkylaryl, and substituted or unsubstituted cyclohexyl. More preferably, $R^2$ and $R^3$ each, independently, are selected from the group consisting of benzyl, cyclohexyl, and substituted or unsubstituted phenyl. More preferably, one of $R^2$ and $R^3$ is $CH_3$ and the other of $R^2$ and $R^3$ is a substituted phenyl. Most preferably, one of $R^2$ and $R^3$ is

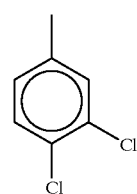

and the other of $R^2$ and $R^3$ is $CH_3$.

Alternatively, $R^2$ and $R^3$ together form a ring structure or a substituted ring structure from 3 to 7 atoms total with 5 or 6 atoms being preferred. Preferably, the ring structure is substituted or unsubstituted carbocycle, substituted or unsubstituted heterocycle, or substituted or unsubstituted cyclohexyl or cyclopentyl. The substituted ring structure can comprise substituents including, but hot limited to, deuterium and halides, including fluorine, chlorine and bromine. A preferred compound having a ring structure formed by $R^2$ and $R^3$ comprises

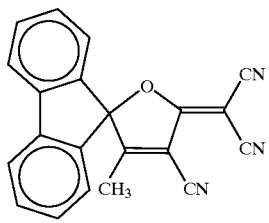

D is an electron donating group as described above.

In other embodiments of the invention, useful compounds are represented by the structure of Formula V:

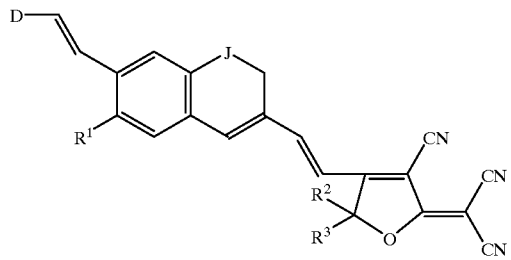

(V)

where, J is $CH_2$, O or S.

Preferably, $R^1$ is —Q—$C_nH_{2n+1}$, —Q—$(CH_2)_aC_nF_{2n+1}$, —Q—$CH_2OCH_2C_nF_{2n+1}$, —Q—$CH_2SCH_2CC_nF_{2n+1}$, —Q—$CH_2OCH_2CF_3$, or —Q—$CH_2SCH_2CF_3$, where n is 1–10, a is 0–10, and Q is absent, O or S. In more preferred embodiments of the invention, $R^1$ is $C_4$–$C_{10}$ or fluorine substituted $C_4$–$C_{10}$. More preferred compounds of this embodiment are represented by the structure of Formula V':

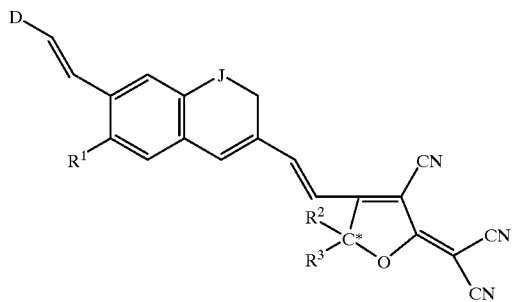

(V')

where, $R^2$ and $R^3$ are further characterized in that they define a ring in which * denotes a spiro junction, or where * denotes a chiral center.

Preferably, $R^2$ and $R^3$ each, independently, are selected from the group consisting of, but not limited to, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, $(CH_2)_n$—O—$(CH_2)_n$ where n is 1–10, and the like. More preferably, $R^2$ and $R^3$ each, independently, are selected from the group consisting of substituted or unsubstituted aryl, substituted or unsubstituted alkylaryl, and substituted or unsubstituted cyclohexyl. More preferably, $R^2$ and $R^3$ each, independently, are selected from the group consisting of benzyl, cyclohexyl, and substituted or unsubstituted phenyl. More preferably, one of $R^2$ and $R^3$ is $CH_3$ and the other of $R^2$ and $R^3$ is a substituted phenyl. Most preferably, one of $R^2$ and $R^3$ is

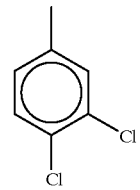

and the other of $R^2$ and $R^3$ is $CH_3$.

Alternatively, $R^2$ and $R^3$ together form a ring structure or a substituted ring structure from 3 to 7 atoms total with 5 or 6 atoms being preferred. Preferably, the ring structure is substituted or unsubstituted carbocycle, substituted or unsubstituted heterocycle, or substituted or unsubstituted cyclohexyl. The substituted ring structure can comprise substituents including, but not limited to, deuterium and halides, including fluorine, chlorine and bromine. A preferred compound having a ring structure formed by $R^2$ and $R^3$ comprises

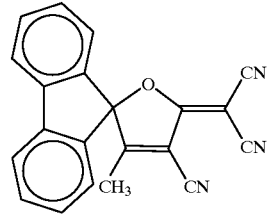

D is an electron donating group as described above.

The present invention is also directed, in part, to optical waveguides comprising polymeric this films having comprising the chromophores of the invention. In preferred embodiments of the invention, optical waveguides comprising a thin film medium have Formula VI:

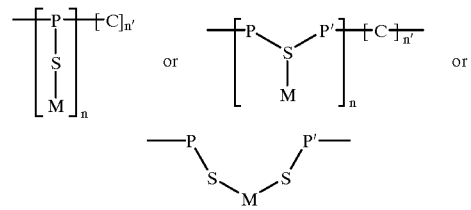

VI

P and P' are polymer main chain units, which can be the same mer unit or different mer unit, and C is a comonomer unit where n is an integer greater than zero and n' is 0 or an integer greater than zero. Polymers and copolymers that may be employed in the present invention are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety. The polymers of the invention can be a homopolymer or a copolymer. Preferred polymers and copolymers include, but are not limited to, acrylate, vinyl carboxylate, substituted arylvinyl, vinyl halide, vinyl carboxylate, alkene, alkadiene, arylvinyl, methacrylate, vinyl chloride, vinyl acetate, vinyl ether, ethylene, propylene, isobutylene, 1-butene, isoprene, styrene, and the like.

Preferably, the polymers of the invention comprise an external field-induced orientation and alignment of pendant side chains. Preferably, the polymer main chain can be a structural type such as polyvinyl, polyoxyalkylene, polysiloxane, polycondensation, and the like. A polymer can be applied to a supporting substrate by conventional means, such as spin coating, dip coating, spraying, Langmuir-Blodgett deposition, and the like. Thin film optical waveguide medium of the present invention after fabrication can be subjected to an external field to orient and align uniaxially the polymer side chains. In one method the polymer medium is heated close to or above the polymer glass transition temperature $T_g$, then an external field (e.g., a DC electric field) is applied to the medium of mobile chromophore molecules to induce uniaxial molecular alignment of the chromophore polymer side chains or guests in a guest-host system parallel to the applied field, and the medium is cooled while maintaining the external field effect.

S is a pendant spacer group having a linear chain length of between about 2–12 atoms. Pendant spacer groups that may be employed in the present invention are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety.

M is a chromophore compound having Formula I, Formula II, Formula III, Formula IV, or Formula V, described above.

The present invention is also directed, in part, to optical devices comprising the optical waveguides of the invention. Optical devices are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety. Preferred optical devices include, but are not limited to, laser frequency converters, optical interferometric waveguide gates, wideband electrooptical guided wave analog-to-digital converters, optical parametric devices, and the like, as described in U.S. Pat. No. 4,775,215, which is incorporated herein by reference in its entirety.

The invention is further illustrated by way of the following examples which are intended to elucidate the invention. These examples are not intended, nor are they to be construed, as limiting the scope of the disclosure.

EXAMPLES

Example 1

General Synthesis of Dicyanomethylenedihydrofurans

To a solution of 0.33 mol of ethyl vinyl ether in 150 ml of dry THF, 0.3 mol of t-BuLi in pentane was added dropwise at −78° C. The mixture was stirred and allowed to warm up slowly to 0° C. and subsequently cooled to −78° C. again. Next, 0.25 mol of cyclohexyl phenyl ketone dissolved in a minimum of dry THF was added dropwise. The mixture was stirred overnight at room temperature, then acidified using HCl/MeOH/THF/H₂O solution to pH 1–4. After stirring this mixture for two hours, most of the solution was evaporated using a rotary evaporator. The remaining mixture was extracted with ethyl ether (3×100 ml). The organic solution was washed with NaHCO₃, brine, and DI water. This mixture was then dried over anhydrous MgSO₄. After evaporating the ether, the crude product was purified by column chromatography (5% ethyl acetate in hexane) to give pure alpha-hydroxy ketone (30 g).

The hydroxy ketone synthesized above (0.02 mol) was mixed with malononitrile (0.04 mol) in ethyl alcohol at 20% w/v based on malononitrile cooled in an ice bath. To this, 20 ml of 1 M NaOC₂H₅/EtOH was added dropwise. The mixture was allowed to stir overnight. After neutralization by concentrated HCl to pH 6, the solvent was evaporated by vacuum. The residue was dissolved into CH₂Cl₂ and filtered to remove the undissolved solid. After evaporating the CH₂Cl₂, the crude product was purified by recrystalization from ethanol to give the dicyanomethylenedihydrofuran compound (1.25 g).

Alternatively, and more preferably, the hydroxy ketone synthesized above (0.02 mol) was mixed with malononitrile (0.04 mol) and potassium carbonate (0.02 mol) in THF (40 ml) and EtOH (2 ml). To this mixture, a catalytic amount of 18-crown ether was added. The mixture was stirred and allowed to reflux overnight. The solid was filtered off, followed by evaporation of most of the solvent. The crude mixture was purified by colum chromatography (CH₂Cl₂) to give the dicyanomethylenedihydrofuran compound (1.5 g) shown below (melting point, MP=194–196° C.).

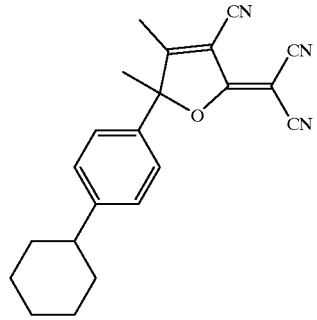

Example 2

Preparation of a Dicyanomethylenedihydrofuran-based Electron Acceptor

To a solution of ethylvinylether (28.8 g in 300 ml of THF) was added 176 ml of t-BuLi dropwise at −78° C. The mixture was slowly warmed to 0° C. and subsequently cooled to −78° C. again. Cyclohexanone (30 g in 30 ml of THF) was added dropwise and the mixture was slowly warmed to room temperature and stirred for an additional four hours. A solution of methanol (70 ml), water (20 ml) and conc. HCl (10 ml) was slowly added to the reaction mixture until a pH of about 2–3 was obtained. The mixture was stirred overnight and neutralized to pH 7 by addition of a 20% solution of NaHCO₃ in water and the solvent was evaporated. The residual solvent was extracted by ether (3×100 ml). The ether solution was washed with NaHCO₃ (50 ml), brine (100 ml), and dried over anhydrous MgSO₄. After removal of the ether, vacuum distillation of the intermediate yielded 36 g.

CH$_2$(CN)$_2$ (13.2 g) and a 1 M solution of NaOC$_2$H$_5$ (0.1 mole) were mixed in an ice bath. Approximately 14.2 g of the intermediate prepared as described above and dissolved in a minimum of EtOH was added dropwise and stirred overnight at room temperature. The mixture was neutralized by 8 ml of conc. HCl to a pH of 6.0 and the solid material was filtered off and the remaining solution was evaporated. The residue from the solution was dissolved into CH$_2$Cl$_2$, filtered again, followed by evaporating the CH$_2$Cl$_2$. The rest of the mixture was recrystalized from ethanol (150 ml) to give 6.1 g of the final compound shown below (mMP= 239–241° C.).

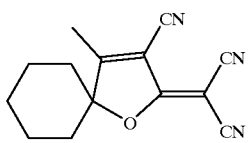

Example 3

Preparation of a Dicyanomethylenedihydrofuran-based Electron Acceptor

To a solution of ethylvinylether (21.6 g in 300 ml of THF) was added 110 ml of t-BuLi dropwise at −78° C. The mixture was warmed to 0° C. and subsequently cooled to −78° C. again. 5',4'-dichloroacetophenone (30.5 g) was dissolved into 150 ml of THF and then added dropwise. This mixture was run overnight at room temperature. A solution of HCl (10 ml), methanol (70 ml), and water (20 ml) was added to the reaction the next day. The mixture was adjusted to pH 4 and allowed to stir overnight. NaHCO$_3$ was added to neutralize this solution to pH 7. The mixture was extracted by ether (3×100 ml). The combined organic acid mixture was washed with NaHCO$_3$ (50 ml), brine (100 ml), and dried over anhydrous MgSO$_4$. Vacuum distillation of the intermediate yielded 55 g.

CH$_2$(CN)$_2$ (13.2 g) and a 1 M solution of NaOC$_2$H$_5$ (0.1 mole) were mixed in an ice bath. Approximately 15 g of the intermediate prepared as described above and dissolved in EtOH was added dropwise and stirred overnight at room temperature. The mixture was neutralized by 8 ml of conc. HCL to a pH of 6.0 and the solid material was filtered and the resulting solution evaporated. The residue was dissolved into CH$_2$Cl$_2$, filtered again, followed by evaporating the CH$_2$Cl$_2$. The rest of the mixture was recrystalized from ethanol (150 ml) to give 5.5 g of the final compound shown below (MP=110–111° C.; 152–153° C.; and 222–224° C., respectively left to right).

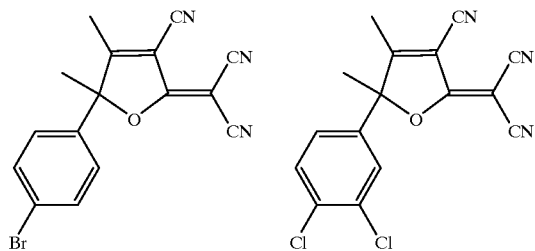

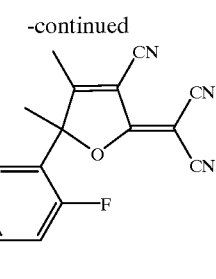

Example 4

Preparation of Trans-[(N,N-di(2-ethanol)amino) phenylene-3-decanyl-2-thiophene]

To a solution of 3-decanyl-2-methyltributylphosphonium-thiophene bromide (26 g, 0.05 mol) and N,N-di-ethanol aminophenyl aldehyde (12.6 g, 0.06 mol) in 200 ml of ethanol, NaOC$_2$H$_5$ (1 M in ethanol) was added dropwise. The resulting mixture was refluxed for 98 hours. After removal of this reaction from the bath oil, the solvent was evaporated, and the residue was extracted with ethyl ether (3×150 ml). The combined ether mixture was washed with water (100 ml), brine (2×100 ml) and dried over anhydrous MgSO$_4$. After removal of the solvent, the residue was purified by column chromatography on silica and eluted using 50% ethyl acetate, 10% acetone, and 40% hexane to give the pure title compound with a yield of 16 g. Carbon and proton NMR were consistent with the structure.

Example 5

Preparation of Trans-[(N,N-di(2-ethanol)amino) phenylene-2-thiene-3-decanyl-5-al]

To a 500 ml flask with the compound synthesized above (10.44 g, 0.0243 mol), 200 ml of THF was added. The solution was cooled to −78° C. and n-BuLi (32 ml, 2.5 M in hexane) was added dropwise. The mixture was stirred for 2 hours followed by addition of DMF (6 ml). The resulting solution was stirred overnight at room temperature. After adding HCl (2 M, 50 ml) and stirring for an hour, the THF was evaporated. The residue was extracted with ethyl ether (3×100 ml). The combined organic solution was washed with saturated Na$_2$CO$_3$ solution (50 ml), water (106 ml), brine (100 ml) and dried over anhydrous MgSO$_4$. After evaporating the solvent, solid target compound (11.1 g, mp 107–109° C.) was obtained. HNMR showed that this compound was pure enough for the next step.

Example 6

Preparation of Chromophore

The above aldehyde compound (3 g, 6.54 mmol) and 2-dicyanomethylen-3-cyano-4,5-dimethyl-5-(3,4-dichlorophenyl)-2,5-dihydrofuran (2.4 g, 7.27 mmol) were mixed and dissolved in EtOH (30 ml). Two or three drops of piperidine were added. The mixture was refluxed for 48 hours. After cooling, the precipitated solid was filtered, recrystalized from EtOH, and purified by chromatography silica elution solvent to give 3.38 g of the chromophore. Carbon and proton NMR were perform ed and analysis thereof was consistent with the structure.

Example 7

Preparation of Chromophore

Trans-[(N,N-di(2-ethanol)amino)phenylene-3,4-dibutyl-2-thiophene-5-al] (0.3 g, 0.7 mmol) is mixed with 2-dicyanomethylen-3-cyano-4,5-dimethyl-5-(3,4-dichlorophenyl)-2,5-dihydrofurane (0.23 g, 0.7 mmol) in EtOH (20 ml). Two or three drops of piperidine is added. The mixture is refluxed for 48 hours. After cooling, the precipitated solid is filtered, recrystalized from EtOH, and purified by chromatography silica elution solvent.

Example 8

Preparation of Highly Chlorinated Electro-Optic Polymer

To a three-neck flask with 1,4,5,6,7,7-hexchloro-5-norbornene-2,3-dicarboxylic acid chloride (2.65 g, 6.23 mmol) and 2,3,5,6-tetrachloro-p-xylene-αα-diol (1.36 g, 4.93 mmol), 2-dicyanomethylen-3-cyano-4-{2-[E-(4-N,N-di-(2-ethanol)amino)phenylene-(3-decanyl)thien-5]-E-vinyl}-5-methyl-5-(3,4-dichlorophenyl)-2,5-dihydrofuran (1 g, 1.3 mmol) were mixed in 20 ml THF at 70° C. Et$_3$N (1.26 g in 15 ml THF) was added dropwise. The mixture was refluxed under Ar for 48 hours. After evaporating some of the THF, the rest of the solution was slowly dropped into MeOH (300 ml) and water (50 ml) with violent stirring. The precipitated solid was filtered, redissolved in THF and precipitated again in MeOH (300 ml). The collected solid was vacuum dried for 8 hours and weighed 4.5 g. The polymer was characterized by DSC and TGA. The $T_g$ is 152° C., and the decomposing temperature under air is 285° C.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A compound having Formula I':

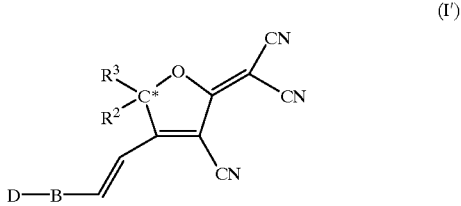

(I')

where:
R$^2$ and R$^3$ define a ring in which * denotes a spiro junction, or where * denotes a chiral center; wherein:
D is an electron donating group;
B is or contains at least one bivalent aromatic ring; and
R$^2$ and R$^3$ each, independently, are either substituted or unsubstituted C$_1$–C$_{10}$ alkyl, substituted or unsubstituted C$_2$–C$_{10}$ alkenyl, substituted or unsubstituted C$_2$–C$_{10}$ alkynyl, substituted or unsubstituted aryl, substituted or unsubstituted alkylaryl, substituted or unsubstituted carbocyclic, substituted or unsubstituted heterocyclic, substituted or unsubstituted cyclohexyl, or (CH$_2$)$_n$—O—(CH$_2$)$_n$, where n is 1–10.

2. The compound of claim 1 wherein D is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

3. The compound of claim 2 wherein B is selected from the group consisting of

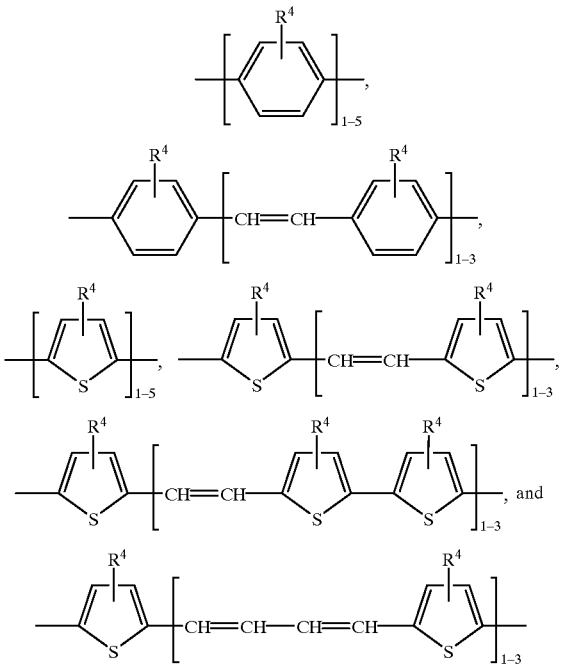

where R$^4$ is H, OH, C$_1$–C$_{10}$ alkyl, alkenyl, alkynyl, or halogen.

4. The compound of claim 3 wherein R$^2$ and R$^3$ each, independently, are selected from the group consisting of, substituted or unsubstituted C$_1$–C$_{10}$ alkyl, substituted or unsubstituted C$_2$–C$_{10}$ alkenyl, substituted or unsubstituted C$_2$–C$_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and (CH$_2$)$_n$—O—(CH$_2$)$_n$ where n is 1–10.

5. The compound of claim 4 wherein R$^2$ and R$^3$ each, independently, are selected from the group consisting of substituted or unsubstituted aryl, substituted or unsubstituted alkylaryl, substituted or unsubstituted carbocycle, substituted or unsubstituted heterocycle, and substituted or unsubstituted cyclohexyl.

6. The compound of claim 5 wherein R$^2$ and R$^3$ each, independently, are selected from the group consisting of benzyl, cyclohexyl, cyclopentyl, and substituted or unsubstituted phenyl.

7. The compound of claim 6 wherein one of R$^2$ and R$^3$ is CH$_3$ and the other of R$^2$ and R$^3$ is a substituted phenyl.

8. The compound of claim 7 wherein the substituted phenyl is

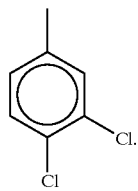

9. The compound of claim 3 wherein R$^2$ and R$^3$ together form a ring structure or a substituted ring structure.

10. The compound of claim 9 wherein R$^2$ and R$^3$ together form cyclohexyl or cyclopentyl.

11. An optical waveguide comprising a thin film medium having Formula VI

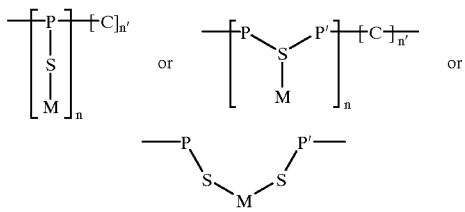

wherein:
P and P' are polymer main chain units;
C is a comonomer unit;
S is a pendant spacer group having a linear chain length of between about 2–12 atoms;
n is an integer greater than zero;
n' is 0 or an integer greater than zero; and
M is a compound of claim 1.

12. An optical device comprising the optical waveguide of claim 11.

13. The optical device of claim 12 wherein said device is selected from the group consisting of a laser frequency converter, an optical interferometric waveguide gate, a wideband electrooptical guided wave analog-to-digital converter, and an optical parametric device.

14. A compound having Formula IV'

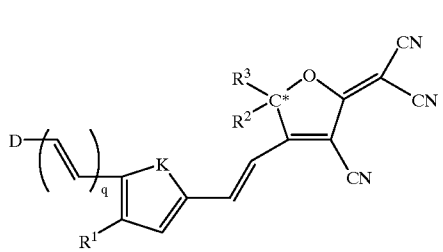

where:
$R^2$ and $R^3$ define a substituted or unsubstituted ring structure in which * denotes a spiro junction, or where * denotes a chiral center;
D is an electron donating group;
K is O or S;
$R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S;
q is 1, 2, or 3; and
$R^2$ and $R^3$ each, independently, are selected from the group consisting of substituted or unsubstituted $C_1-C_{10}$ alkyl, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10.

15. The compound of claim 14 wherein D is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

16. The compound of claim 15 wherein $R^2$ and $R^3$ each, independently, are selected from the group consisting of substituted or unsubstituted $C_1-C_{10}$ alkyl, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10.

17. The compound of claim 16 wherein $R^2$ and $R^3$ each, independently, are selected from the group consisting of substituted or unsubstituted aryl, substituted or unsubstituted alkylaryl, and substituted or unsubstituted cyclohexyl or cyclopentyl.

18. The compound of claim 17 wherein $R^2$ and $R^3$ each, independently, are selected from the group consisting of benzyl, cyclohexyl, cyclopentyl, and substituted or unsubstituted phenyl.

19. The compound of claim 18 wherein one of $R^2$ and $R^3$ is $CH_3$ and the other of $R^2$ and $R^3$ is a substituted phenyl.

20. The compound of claim 19 wherein the substituted phenyl is

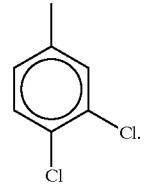

21. The compound of claim 16 wherein a is 1–3 and n is 1–3.

22. The compound of claim 21 wherein $R^1$ is $C_4-C_{10}$ or fluorine substituted $C_4-C_{10}$.

23. The compound of claim 15 wherein $R^2$ and $R^3$ together form cyclohexyl or cyclopentyl.

24. The compound of claim 23 wherein a is 1–3 and n is 1–3.

25. The compound of claim 24 wherein $R^1$ is $C_4-C_{10}$ or fluorine substituted $C_4-C_{10}$.

26. A compound having Formula V'

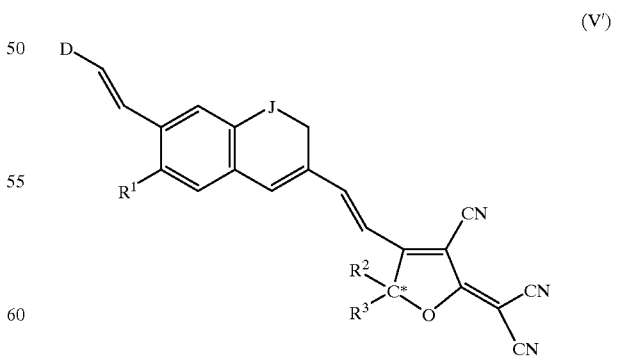

where:
$R^2$ and $R^3$ define a substituted or unsubstituted ring structure in which * denotes a spiro junction, or where * denotes a chiral center;

D is an electron donating group;

J is $CH_2$, O or S;

$R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S; and $R^2$ and $R^3$ each, independently, are selected from the group consisting of substituted or unsubstituted $C_1-C_{10}$ alkyl, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10.

27. The compound of claim 26 wherein D is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

28. The compound of claim 27 wherein $R^2$ and $R^3$ each, independently, are selected from the group consisting of, substituted or unsubstituted $C_1-C_{10}$ alkyl, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10.

29. The compound of claim 28 wherein $R^2$ and $R^3$ each, independently, are selected from the group consisting of substituted or unsubstituted aryl, substituted or unsubstituted alkylaryl, substituted or unsubstituted carbocycle, substituted or unsubstituted heterocycle, and substituted or unsubstituted cyclohexyl.

30. The compound of claim 29 wherein $R^2$ and $R^3$ each, independently, are selected from the group consisting of benzyl, cyclohexyl, cyclopentyl, and substituted or unsubstituted phenyl.

31. The compound of claim 30 wherein one of $R^2$ and $R^3$ is $CH_3$ and the other of $R^2$ and $R^3$ is a substituted phenyl.

32. The compound of claim 31 wherein the substituted phenyl is

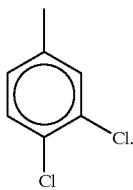

33. The compound of claim 32 wherein a is 1–3 and n is 1–3.

34. The compound of claim 33 wherein $R^1$ is $C_4-C_{10}$ or fluorine substituted $C_4-C_{10}$.

35. The compound of claim 27 wherein $R^2$ and $R^3$ together form a ring structure or a substituted ring structure.

36. The compound of claim 35 wherein $R^2$ and $R^3$ together form cyclohexyl or cyclopentyl.

37. The compound of claim 36 wherein a is 1–3 and n is 1–3.

38. The compound of claim 37 wherein $R^1$ is $C_4-C_{10}$ or fluorine substituted $C_4-C_{10}$.

39. An optical waveguide comprising a thin film medium having Formula VI

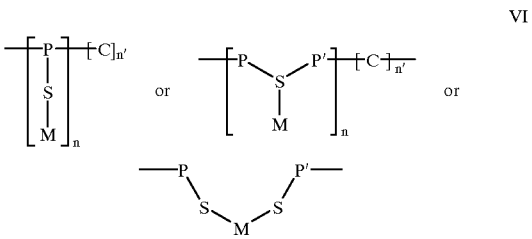

wherein:

P and P' are polymer main chain units;

C is a comonomer unit;

S is a pendant spacer group having a linear chain length of between about 2–12 atoms;

n is an integer greater than zero;

n' is 0 or an integer greater than zero; and

M is a compound of claims 14 or 27.

40. An optical device comprising the optical waveguide according to claim 39.

41. The optical device of claim 40 wherein said device is selected from the group consisting of a laser frequency converter, an optical interferometric waveguide gate, a wideband electrooptical guided wave analog-to-digital converter, and an optical parametric device.

42. A method of preparing an electron withdrawing group having the formula:

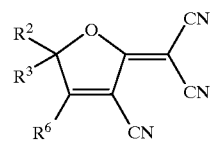

wherein:

$R^2$ and $R^3$ each, independently, are selected from the group consisting of H, substituted and unsubstituted $C_1-C_{10}$ alkyl, substituted and unsubstituted $C_2-C_{10}$ alkenyl, substituted and unsubstituted $C_2-C_{10}$ alkynyl, substituted and unsubstituted aryl, substituted and unsubstituted alkylaryl, substituted and unsubstituted carbocycles, substituted and unsubstituted heterocycles, substituted and unsubstituted cyclohexyl, and $(CH_2)_n-O-(CH_2)_n$ where n is 1–10; or $R^2$ and $R^3$ together form a ring structure or a substituted ring structure; and $R^6$ is substituted or unsubstituted $C_1-C_4$ alkyl, substituted or unsubstituted $C_2-C_4$ alkenyl, or substituted or unsubstituted $C_2-C_4$ alkynyl, said method comprising the steps:

(a) providing an alkylvinylether;

(b) contacting said alkylvinylether with a strong base to form a first intermediate compound;

(c) contacting said first intermediate compound with a ketone to form a second intermediate compound; and (d) reacting said second intermediate compound with dicyanomethane in the presence of a second base to form said electron withdrawing group.

43. The method of claim 42 wherein said alkylvinylether is in a solvent.

44. The method of claim 43 wherein said solvent is tetrahydrofuran or 1,4-dioxane.

45. The method of 44 wherein said alkylvinylether comprises the formula $CH_3-(CH_2)_x-O-CH=CHR^6$, where x is 1–3 and $R^6$ is H or $C_1-C_4$ alkyl.

46. The method of claim 45 wherein said alkylvinylether is methylvinylether or ethylvinylether.

47. The method of claim 42 wherein said strong base has a $pK_a$ greater than the ethylinic C—H bond α to the oxygen function of said alkylvinylether.

48. The method of claim 47 wherein said strong base is an alkyl lithium.

49. The method of claim 48 wherein said alkyl lithium is t-BuLi or sec-BuLi.

50. The method of claim 42 wherein said ketone comprises the formula $R^3-C(=O)R^2$, wherein $R^2$ and $R^3$ each, independently are selected from the group consisting of H, substituted o unsubstituted $C_1-C_{10}$ alkyl, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10.

51. The method of claim 50 wherein said $R^2$ and $R^3$ each, independently, are selected from the group consisting of benzyl, cyclohexyl, cyclopentyl, phenyl, and substituted phenyl.

52. The method of claim 51 wherein one of said $R^2$ and $R^3$ is $CH_3$ and the other of $R^2$ and $R^3$ is a substituted phenyl.

53. The method of claim 42 wherein said second base is a metal alkoxide.

54. The method of claim 53 wherein said metal alkoxide is $NaOC_2H_5$.

55. The method of claim 42 wherein said electron withdrawing group has the formula:

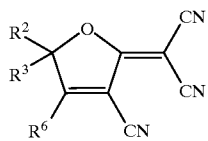

wherein:
$R^2$ and $R^3$ each, independently, are selected from the group consisting of substituted and unsubstituted $C_1-C_{10}$ alkyl, substituted and unsubstituted $C_2-C_{10}$ alkenyl, substituted and unsubstituted $C_2-C_{10}$ alkynyl, substituted and unsubstituted aryl, substituted and unsubstituted alkylaryl, substituted and unsubstituted carbocycles, substituted and unsubstituted heterocycles, substituted and unsubstituted cyclohexyl, and $(CH_2)_n-O-(CH_2)_n$ where n is 1–10; or $R^2$ and $R^3$ together form a ring structure or a substituted ring structure; and $R^6$ is substituted or unsubstituted $C_1-C_4$ alkyl, substituted or unsubstituted $C_2-C_4$ alkenyl, or substituted or unsubstituted $C_2-C_4$ alkynyl.

56. The method of claim 55 wherein said ketone comprises the formula $R^3-C(=O)R^2$, wherein $R^2$ and $R^3$ each, independently, are selected from the group consisting of substituted or unsubstituted $C_1-C_{10}$ alkyl, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted and unsubstituted carbocycle, substituted or unsubstituted heterocycle, substituted or unsubstituted cyclohexyl, and $(CH_2)_n-O-(CH_2)_n$ where n is 1–10.

57. A compound having Formula I

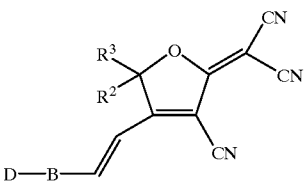

(I)

wherein:
D is an electron donating group;
B comprises at least one bivalent ring; and
$R^2$ and $R^3$ each, independently, are selected from the group consisting of substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10.

58. The compound of claim 57 wherein D is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

59. The compound of claim 57 wherein B is selected from the group consisting of

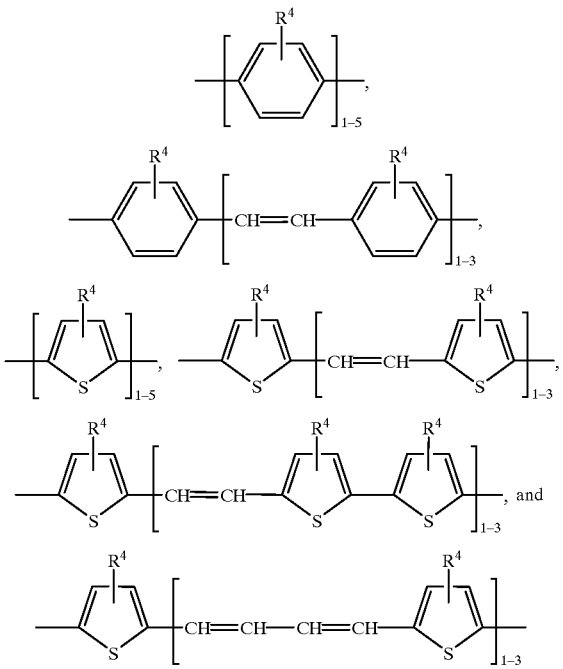

where $R^4$ is H, OH, $C_1-C_{10}$ alkyl, alkenyl, alkynyl, or halogen.

60. The compound of claim 59 wherein $R^2$ and $R^3$ each, independently, are selected from the group consisting of benzyl, cyclohexyl, cyclopentyl, and substituted or unsubstituted phenyl.

61. The compound of claim 57 wherein $R^2$ and $R^3$ together form a ring structure or a substituted ring structure.

62. The compound of claim 61 wherein $R^2$ and $R^3$ together form cyclohexyl or cyclopentyl.

63. A compound having Formula IV $$(IV)$$

wherein:
D is an electron donating group;
K is O or S;
$R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2C_nF_{2n+1}$, $-Q-CH_2OCH_2CF_3$, or $-Q-CH_2SCH_2CF_3$, where n is 1–10, a is 0–10, and Q is absent, O or S;
q is 1, 2, or 3; and
$R^2$ and $R^3$ each, independently, are selected from the group consisting of, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10; or $R^2$ and $R^3$ together form a ring structure or a substituted ring structure.

64. The compound of claim 63 wherein D is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

65. The compound of claim 63 wherein $R^2$ and $R^3$ each, independently, are selected from the group consisting of benzyl, cyclohexyl, cyclopentyl, and substituted or unsubstituted phenyl.

66. The compound of claim 63 wherein $R^1$ is $C_4-C_{10}$ or fluorine substituted $C_4-C_{10}$.

67. The compound of claim 63 wherein $R^2$ and $R^3$ together form cyclohexyl or cyclopentyl.

68. The compound of claim 63 wherein a is 1–3 and n is 1–3.

69. A compound having Formula V $$(V)$$

D is an electron donating group;
J is $CH_2$, O or S;
$R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S; and $R^2$ and $^3$ each, independently, are selected from the group consisting of, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10.

70. The compound of claim 69 wherein D is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

71. The compound of claim 69 wherein $R^2$ and $R^3$ each, independently, are selected from the group consisting of substituted or unsubstituted aryl, substituted or unsubstituted alkylaryl, substituted or unsubstituted carbocycle, substituted or unsubstituted heterocycle, and substituted or unsubstituted cyclohexyl.

72. The compound of claim 71 wherein $R^2$ and $R^3$ each, independently, are selected from the group consisting of benzyl, cyclohexyl, cyclopentyl, and substituted or unsubstituted phenyl.

73. The compound of claim 69 wherein a is 1–3 and n is 1–3.

74. The compound of claim 69 wherein $R^1$ is $C_4-C_{10}$ or fluorine substituted $C_4-C_{10}$.

75. The compound of claim 69 wherein $R^2$ and $R^3$ together form a ring structure or a substituted ring structure.

76. An optical waveguide comprising a thin film medium having Formula VI $$(VI)$$

wherein:
P and P' are polymer main chain units;
C is a comonomer unit;
S is a pendant spacer group having a linear chain length of between about 2–12 atoms;
n is an integer greater than zero;
n' is 0 or an integer greater than zero; and
M is a compound according to any one of claims 57, 59, 63–68, or 69–72.

77. An optical device comprising the optical waveguide according to claim 76.

78. The optical device of claim 77 wherein said device is selected from the group consisting of a laser frequency converter, an optical interferometric waveguide gate, a wideband electrooptical guided wave analog-to-digital converter, and an optical parametric device.

* * * * *